(12) United States Patent
Hecht et al.

(10) Patent No.: US 6,303,299 B1
(45) Date of Patent: *Oct. 16, 2001

(54) VITRO SUPPRESSION AS A TOOL FOR THE INVESTIGATION OF TRANSLATION INITIATION

(75) Inventors: Sidney M. Hecht, Charlottesville; Vladimir Karginov, Ashburn; Andrei V. Karginov, Charlottesville, all of VA (US)

(73) Assignee: University of Virginia Patent Foundation

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/076,804
(22) Filed: May 13, 1998

Related U.S. Application Data
(60) Provisional application No. 60/046,306, filed on May 13, 1997.

(51) Int. Cl.[7] .............................................. C12Q 1/68
(52) U.S. Cl. ........................ 435/6; 435/69.1; 435/440; 436/504; 536/23.1; 536/24.1
(58) Field of Search ................................ 435/69.1, 5, 440; 436/504; 536/23.1, 24.1

(56) References Cited

PUBLICATIONS

Roesser et al., *Biochemistry* 28:5185–5195, 1989.*

Heckler et al., *Biochemistry* 27:7254–7262, 1988.*

* cited by examiner

*Primary Examiner*—Robert D. Budens
(74) *Attorney, Agent, or Firm*—John P. Breen

(57) ABSTRACT

The invention relates to a method for studying translation initiation and for identifying potential inhibitors of translation initiation by expressing proteins in the presence of misacylated suppressor tRNAs.

17 Claims, 11 Drawing Sheets

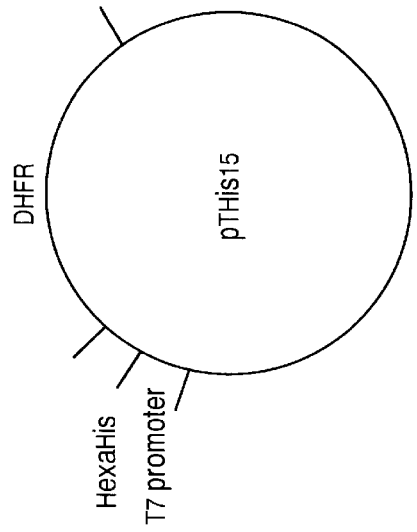
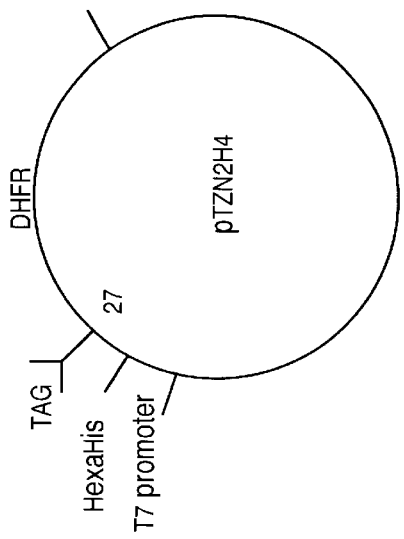
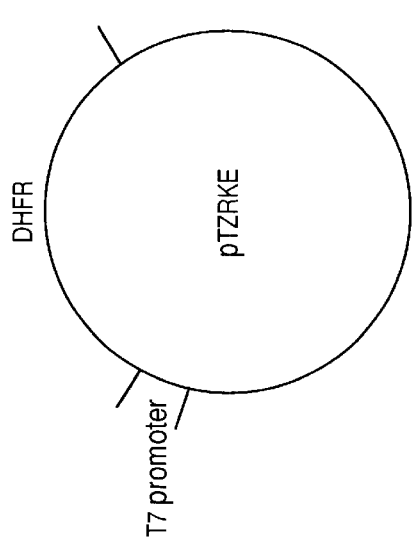
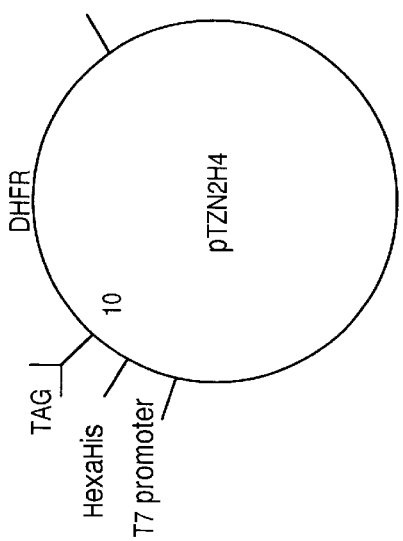

relative intensities
protein1/protein 2      1.5   1.5   1.5   1.5
protein1/protein 3      2.4   3.6   4.4

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:Nonopeptide
      immediately prior to the normal DHFR sequence

<400> SEQUENCE: 1

Met Ile His His His His His His Glu
 1               5

<210> SEQ ID NO 2
<211> LENGTH: 117
<212> TYPE: DNA
<213> ORGANISM: Artificial Sequence
<220> FEATURE:
<223> OTHER INFORMATION: Description of Artificial Sequence:DNA template
      used for in vitro runoff transcription

<400> SEQUENCE: 2
aattctaata cgactcacta tagggctat agctcagctg ggagagcgct tgcatctaaa      60
gcaagaggtc agcggttcga tcccgcttag ccccaccagg atccgcatcc ttctgca       117

<210> SEQ ID NO 3
<211> LENGTH: 228
<212> TYPE: DNA
<213> ORGANISM: Artificial Sequence
<220> FEATURE:
<223> OTHER INFORMATION: Description of Artificial Sequence:Nucleotide
      sequence at the 5' end of the DHFR gene

<400> SEQUENCE: 3
aagctttacg tatagtggcg acaatttttt ttatcgggaa tctcaatgat ccaccatcac     60
caccatcacg aaatgatcag tctgattgcg gcgttagcgg tagatcgcgt tatcggcatg    120
gaaaacgcca tgccgtggaa cctgcctgcc gatctcgcct ggtttaaacg caacaccta    180 aataaacccg tgattatggg ccgccatacc tgggaatcaa tcggtcgt                 228

<210> SEQ ID NO 4
<211> LENGTH: 60
<212> TYPE: PRT
<213> ORGANISM: Artificial Sequence
<220> FEATURE:
<223> OTHER INFORMATION: Description of Artificial Sequence
<220> FEATURE:
<223> OTHER INFORMATION: Description of Artificial Sequence:Deduced
      amino acid sequence at the 5' end of the DHFR gene

<400> SEQUENCE: 4

Met Ile His His His His His His Glu Ile Ser Leu Ile Ala Ala Leu
 1               5                  10                  15
```

-continued

```
Ala Val Asp Arg Val Ile Gly Met Glu Asn Ala Met Pro Trp Asn Leu
            20                  25                  30
Pro Ala Asp Leu Ala Trp Phe Lys Arg Asn Thr Leu Asn Lys Pro Val
            35                  40                  45
Ile Met Gly Arg His Thr Trp Glu Ser Ile Gly Arg
    50                  55                  60
```

VITRO SUPPRESSION AS A TOOL FOR THE INVESTIGATION OF TRANSLATION INITIATION

CROSS-REFERENCE TO RELATED APPLICATIONS

This application claims priority under 35 USC §119 (e) to U.S. Provisional Application Ser. No. 60/046,306, May 13, 1997.

GOVERNMENT SUPPORT

This work was supported in part by grant GM43328. from the National Institutes of Health. The government may have certain rights in the invention.

BACKGROUND OF THE INVENTION

1. Field of the Invention

The present invention relates to a method for studying translation initiation and for identifying potential inhibitors of translation initiation. More specifically, it relates to methods in which proteins are expressed in the presence of misacylated suppressor tRNAs.

2. Discussion of the Background

Translation initiation is a key regulatory step in the synthesis of numerous proteins in eukaryotic cells. Different forms of the same protein sometimes with absolutely distinct functions can be produced as a result of alternative initiation of translation (Bullock, et al (1997) *J. Exp. Med.*, 186, 1051–1058; Prats, et al. (1992) *Mol. Cell. Biol.*, 12, 4796–4805; Delmas, et al. (1992) *Proc. Natl. Acad. Sci. USA*, 89, 4226–4230 and Packham, et al. (1997) *Biochem. J.*, 328, 807–813.). Translation reinitiation is involved in regulation of viral life cycle for human immunodefficiency virus type I (Schwartz, et al., (1990) *J. Virol.*, 64, 5448–5456; Schwartz, et al., (1992) *Mol. Cell. Biol.*, 12, 207–219 and Luukkonen, et al., (1995) *J. Virol.*, 69, 4086–4094.).

The current model of translation initiation in eukaryotes postulates that protein synthesis starts at the AUG codon nearest to the 5'-end of the mRNA (Kozak, M. (1987) *Nucleic Acids Res.*, 15, 8125–8148; Kozak, M. (1989), *J. Cell Biol*, 108, 229–241; Kozak, M. (1992), *Crit. Rev. Biochem. Mol. Biol.*, 27, 385–402; Kozak, M. (1986), *Cell*, 44, 283–292; Kozak, M. (1987) *J. Mol. Biol.*, 196, 947–950 and Kozak, M. (1989) *Mol. Cell. Biol.*, 9, 5073–5080.). In some cases, reinitiation of translation can occur at the next AUG codon after termination of protein synthesis (Kozak, M. (1987) Mol. Cell. Biol., 7, 3438–3445; Hinnebusch, A. G. (1990) *Trends Biochem. Sci.*, 15, 148–152 and Kozak, M. (1995) *Proc. Nati. Acad. Sci. USA*, 92, 2662–2666). Another process, called 'leaky scanning', takes place when the 40S ribosomal subunit bypasses the first AUG codon because of a non-optimal context. In this case the ribosomes will start synthesis at the second AUG codon (Kozak, M. (1992) *Crit. Rev. Biochem. Mol. Biol.*, 27, 385–402; Kozak, M. (1986) *Cell*, 44, 283–292; Kozak, M. (1987) *J. Mol. Biol.*, 196, 947–950; Kozak, M. (1989) *Mol. Cell. Biol.*, 9, 5073–5080 and Kozak, M. (1995) *Proc. Natl. Acad. Sci. USA*, 92, 2662–2666).

In spite of the fact that the above-described translation initiation mechanism was shown to predominate for norm eukaryotic mRNAs, some viruses, such as hepatitis C virus (HCV), Moloney murine leukemia virus (MoMuLV), encephalomyocarditis virus (EMCV), foot-and-mouth disease virus (FMDV) and poliovirus, use an unusual internal translation initiation process (Kolupaeva, et al. (1996) *RNA*, 2, 1199–1212; Jang, et al. (1988) *J. Virol.*, 62, 2636–2643; Pellitier, et al. (1988) *Nature*, 334, 320–335; Kuhn, et al. (1990), *J. Virol*, 64, 4625–4631; Tsukiyama-Kohara, et al. (1992) *J. Virol.*, 66, 1476–1483 and Vagner, et al. (1995) *J. Biol. Chem.*, 270, 20376–20383). The same mechanism was recently found for translation of human proto-oncogene c-myc (Nanbru, et al. (1997) *J. Boil. Chem.*, 2272, 32061–32066). In this case, protein synthesis starts far from the 5'-end (more than 400 nucleotides).

A powerful technique of incorporation of synthetic amino acid into a protein at predetermined positions was developed within the last two decades. The method involves incorporation of a stop codon at the position of interest in the protein gene and in vitro expression of the gene in the presence of misacylated suppressor tRNA, the latter of which will allow to readthrough of the stop codon (Hecht, et al. (1978) *J. Biol. Chem.*, 253, 4517–4520; Heckler, et al. (1983), *J. Biol. Chem.*, 258, 4492–4495; Heckler, et al. (1984), *Biochemistry*, 23, 1468–1473; Baldini, et al. (1988) *Biochemistry*, 27, 7951–7959; Bain, et al. (1989) *J Am. Chem. Soc.*, 111, 8013–8014; Roesser, et al. (1989) *Biochemistry*, 28, 5185–5195; Robertson, et al. (1989) *Nucleic Acids Res.*, 17, 9649–9660; Robertson, et al. (1991) *J Am. Chem. Soc.*, 113, 2722–2729; Hecht, S. M. (1992) *Acc. Chem. Res.*, 25, 545–552; Lodder, et al. (1997) *J. Org. Chem.*, 62, 778–779; Noren, et al. (1989) *Science*, 244, 182–188; Bain, et al. (1991) *Tetrahedron*, 47, 2389–2400 and Mamaev., et al. (1996) *J. Am. Chem. Soc.*, 118, 7243–7244). Numerous modified proteins and peptides have been successfully synthesized and studied using this strategy (Noren, et al. (1989) *Science*, 244, 182–188; Bain, et al. (1991) *Tetrahedron*, 47, 2389–2400; Mamaev., et al. (1996) *J. Am. Chem. Soc.*, 118, 7243–7244; Ellman, et al. (1992) *Science*, 255, 197–200; Chung, et al. (1993) *Science*, 259, 806–809; Mendel, et al. (1993) *J Am. Chem. Soc.*, 115, 4359–43360 and Thorson, et al. (1995) *J Am. Chem. Soc.*, 117, 1157–1160). One recent achievement was exploring translation initiation mechanism using an in Vitro suppression method (Karginov, et al. (1997) *Nucleic Acids Res.*, 25, 3912–3916). It was shown that different types of translation initiation (i.e. reinitiation, 'leaky scannings') can be regulated and distinguished by changing of concentration of the misacylated tRNA.

In view of the importance of understanding translation initiation for the development of inhibitors and/or modulators thereof, it is clear that there exists a need in the art for a method for studying translation initiation and for identifying inhibitors of translation initiation.

SUMMARY OF THE INVENTION

Accordingly, one object of this invention is to provide a novel method for analyzing a translation initiation mechanism by:

a. expressing proteins encoded by a nucleic acid in the presence of a misacylated suppressor tRNA;

b. analyzing relative amounts of the proteins produced in (a); and c. comparing the amount of each protein analyzed into (b) to determine the translation initiation site utilized for each protein.

Another object of the invention is to provide a method for identifying inhibitors of translation initiation by:

a. performing the above-noted method in the presence and absence of a potential inhibitor, on a nucleic acid from which translation initiation is to be inhibited;

b. comparing the amount of proteins produced in the presence and absence of the potential inhibitor; and c. correlating a decrease in proteins produced in the presence of the potential inhibitor with the ability of the potential inhibitor to inhibit the translation of the proteins.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 2A–2D depict plasmid constructs used to elaborate mRNAs for the study of the sites of translation initiation of DHFR.

trunslation products purified on DEAE Sepharose; lane 3, translation of "non-optimal" mRNA in the presence of deprotected NBD-Dap-tRNA$^{Phe}_{CUA}$ (crude mixture); lane 4, "optimal" translation product purified on a Ni-NTA column; lane 5, "optimal" translation products purified on DEAE Sepharose; lane 6, translation of "optimal" MnRNA in the presence of deprotected NBD-Dap-tRNA$^{Phe}_{CUA}$ (crude mixture).

Figure 15:
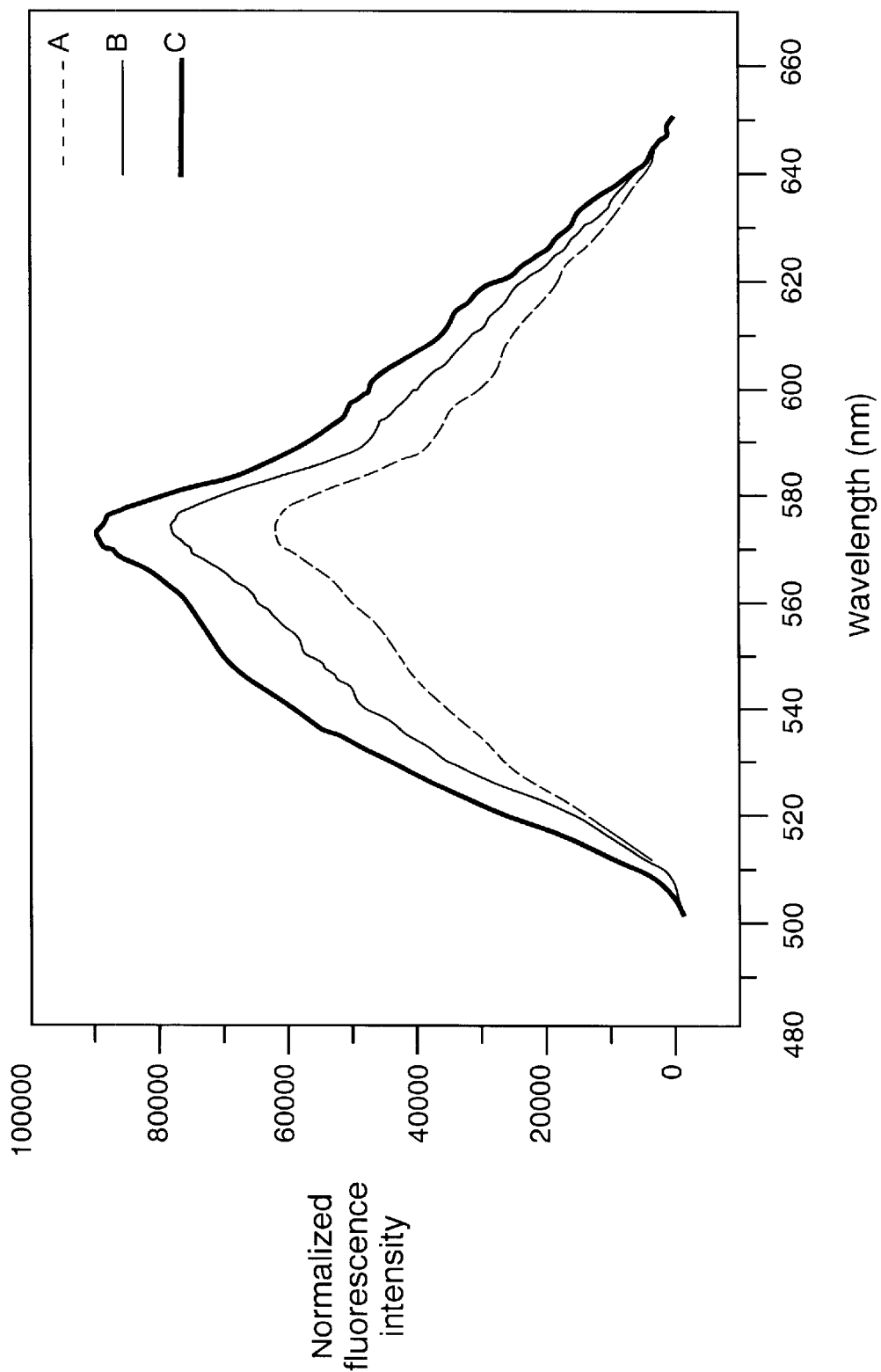

FIG. 15 is the normalized fluorescence emission spectra for purified DHFR, containing NBD-Dap. A. Control purification. A mixture of 200 µL of 70% rabbit reticulocyte lysate with 10 mnol of NBD-Dap-pdCpA was purified on DEAE Sepharose and Ni-NTA agarose by the same procedure used for the translation mixtures. B. "Non-optimal" translation product, purified on DEAE Sepharose and Ni-NTA columns. C. "Optimal" translation product, purified on DEAE and Ni-NTA columns.

Figure 16:
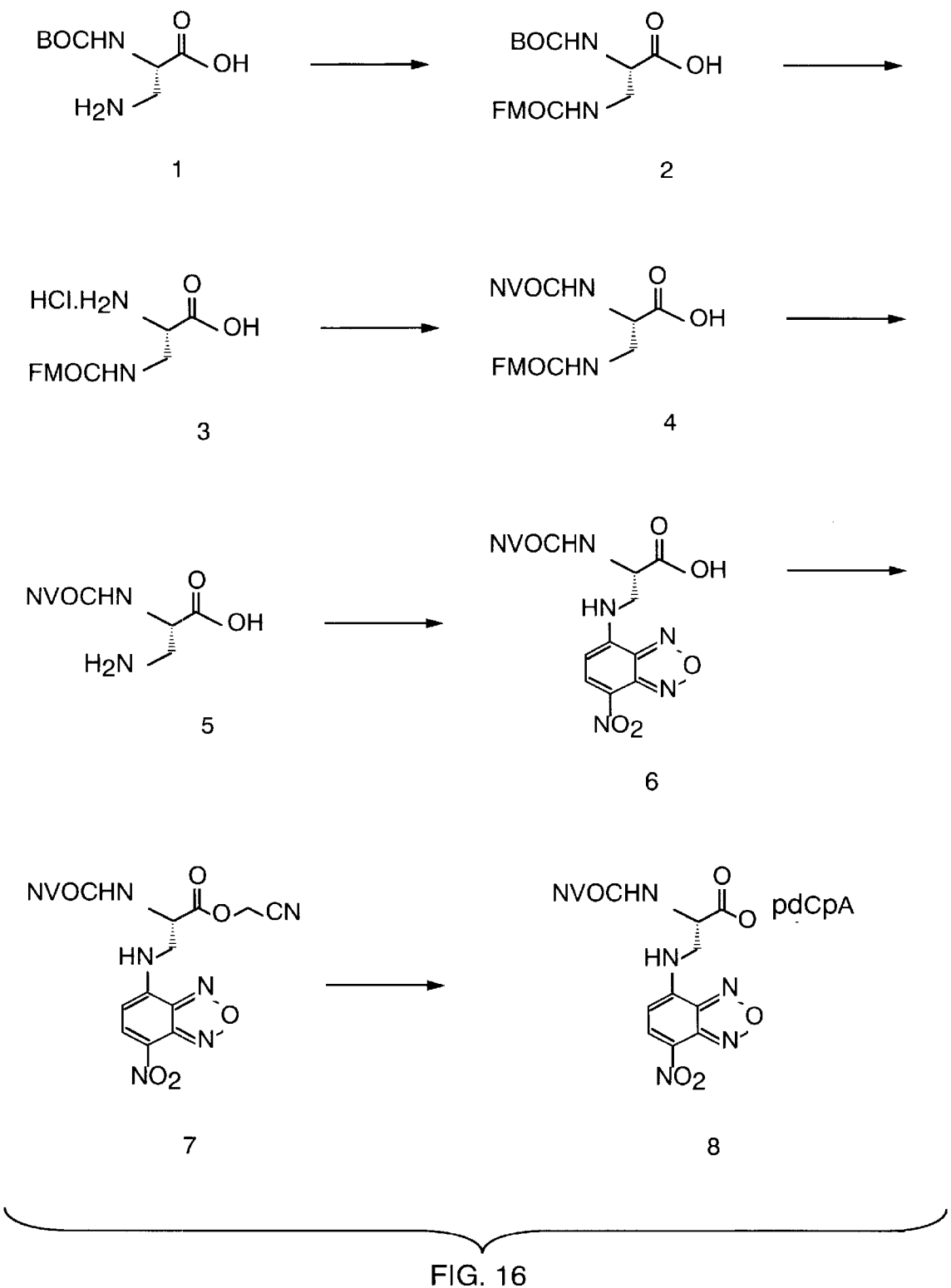

FIG. 16 shows the synthesis of compounds used in the method of the invention.

DESCRIPTION OF THE PREFERRED EMBODIMENTS

The present invention is a method which allows one to study the mechanism of translation initiation in eukaryotic cells and the identification of inhibitors of specific translation initiation mechanisms. The method is based on an in vitro suppression technique and employs misacylated suppressor tRNA. In a preferred embodiment, the suppressor tRNAs are misacylated with a fluorescent compound, preferably 3-N-(7-nitrobenz-2-oxa-1,3-diazol-4-yl)-2,3-diaminopropionic acid (NBD-Dap) in protein synthesis reaction as a marker and regulator of translation. NBD-Dap is a fluorescent amino acid that has been employed for in vitro suppression previously (Hinnebusch (1990) *Trends Biochem. Sci.*, 15, 148–152). When the misacylated suppressor tRNAs are fluorescent, detection of the various proteins is made simple, and is preferably done using a flourescent spectrophotometer. However, any detectable label may be used. Examples of acceptable labels include radiolabels, biotin (which is detected using avidin or strepavidin), chemiluminescent labels, enzyme triggered color labels in ELISA assays, etc.

Any nucleic acid may be used as a template for studying a translation initiation mechanism. The nucleic acid may be modified to introduce particular sequences, such as start codons (AUG), or sequences which alter the context of the AUG (i.e., make it more or less favorable as a site for initiation). In a preferred embodiment, the nucleic acid used for studying the translation initiation mechanism encodes dihydrofolate reductase (DHFR). Any gene that can be expressed at the level of its protein can be suitable; those with an internal ribosome entry site (IRES) such as the 5'-untranslated region of hepatitis C virus are especially promising.

The translation is preferably performed in an in vitro translation system, more preferably in a rabbit reticulocyte lysate or an *E. coli* S-30 coupled transcription—translation system. Other systems are similarly suitable. Wheat germ and baculovirus translation systems may also be used. Such systems may require minor art known modifications which do not constitute an aspect of this invention, per se.

The suppressor tRNA may be from any organism, but is preferably from yeast or *E. coli*. Preferably, the tRNA is yeast tRNA$^{Phe}_{CUA}$ or *E. coli* tRNA$^{Ala}_{CUA}$. The misacylated tRNA is used at a concentration of about 0.05 to 0.4 mg/ml, preferably 0.1 to 0.3 mg/ml, and most preferably about 0.1 mg/ml.

The proteins produced from the translation reaction may be analyzed by any means known by those of ordinary skill in the art which are suitable for separating proteins of different sizes, such as on a gel or using molecular sieve (i.e., size exclusion) chromatography. Preferably the proteins are analyzed by electrophoresis on SDS-PAGE.

After studying the mechanism of translation initiation, the method can be used to identify compounds which stimulate or inhibit, or otherwise modulate translation initiation. This is particularly important in the area of treating viral infection. Another application of the method is the identification of compounds which may stimulate the production of a protein in a patient with otherwise low levels of that protein. With respect to viral infection, the translation systems of human immunodeficiency virus (HIV), hepatitis C virus (HCV), Moloney murine leukemia virus (MoMuLV), encephalomyocarditis virus (EMCV), foot-and-mouth disease virus (FMDV), and poliovirus are particularly amenable to the method. For the treatment of HIV, inhibition of the translation of the transactivating protein, tat, is useful in treating viral infection.

Figure 10:
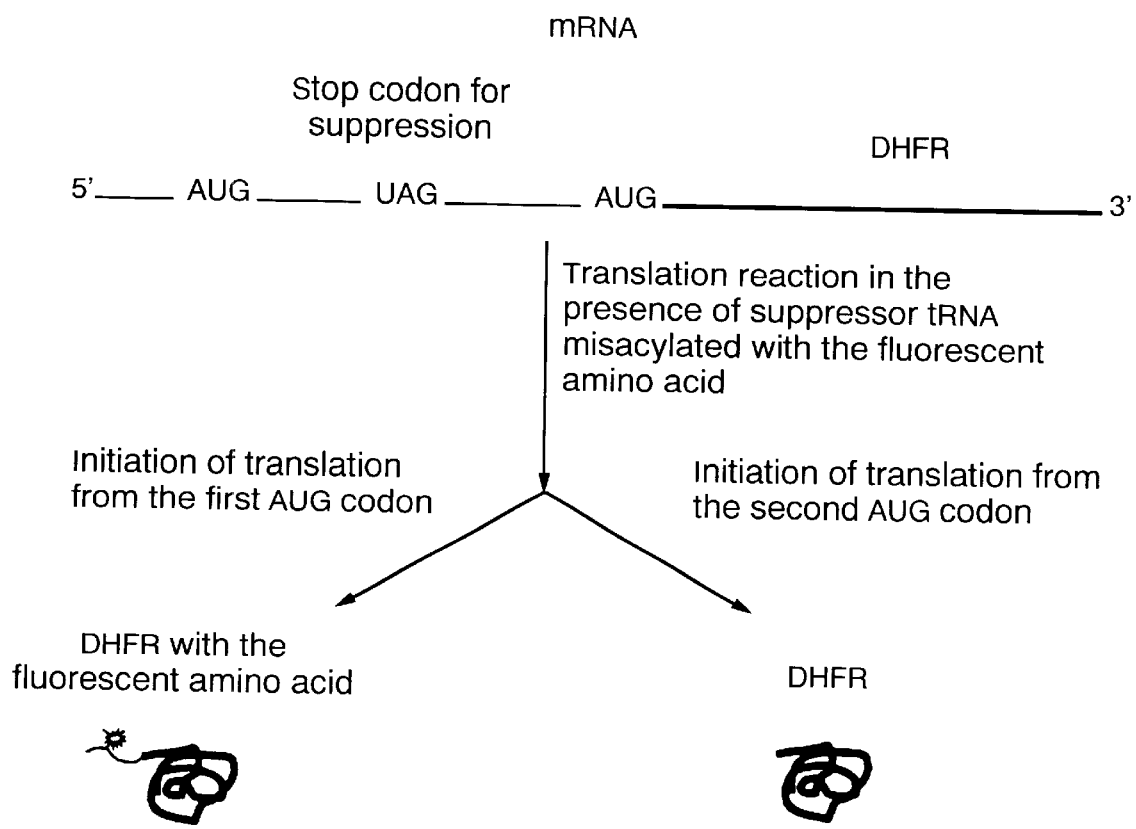
FIG. 10 shows alternative initiation of translation of DHFR. Only full-length translation product gives fluorescence signal.

The main idea is presented in FIG. 10. Initiation of translation at the first AUG codon results in production of fullength dihydrofolate reductase (DHFR) bearing the fluorescent amino acid. Translation from the second AUG codon produces truncated protein, which gives no fluorescent signal. Therefore, by comparing the intensity of the fluorescence signal with the amount of protein produced it is possible to monitor initiation of translation at different sites.

Having generally described this invention, a further understanding can be obtained by reference to certain specific examples which are provided herein for purposes of illustration only and are not intended to be limiting unless otherwise specified.

EXAMPLES

Example 1

Materials and Methods

[$^{35}$S]methionine (1000 Ci/mmol) was purchased from Amersham Corporation. Nuclease-treated rabbit reticulocyte lysate, *E. coli* S-30 extract system for linear templates, wheat germ extract, DNA polymerase I (Klenow fragment), T4 DNA ligase, T7 RNA polymerase and restriction endonucleases were obtained from Promega, Inc. Purified acylated bovine serum albumin (BSA) was from New England Biolabs β-NADPH and dihydrofolate were obtained from Sigma Chemicals. Kits for plasmid isolation and for kpurification of proteins using the Ni-NTA agarose were purchased from QIAGEN, Inc. Synthetic oligonucleotides were obtained from Cruachem, Inc. or Midland Company. *E. coli* competent cells were purchased from Stratagene Cloning Systems. AmpliScribe transcription kits were from Epicentre Technologies.

Ultraviolet spectral measurements were made using a Perkin-Elner Lambda Array 3840 spectrophotometer equipped with a thermal control unit. Radioactivity measurements were made with a Beckman LS-100C liquid scintillation counter. Phosphorimager analysis was performed using a Molecular Dynamics 300E phosphorimager equipped with ImageQuant software.

Construction of plasmids carrying the dihydrofolate reductase (DHFR) gene, construction of plasmids for runoff transcription of yeast tRNA$^{Phe}_{CUA}$ (-CA) and *E. coli* #tRNA$^{Ala}_{CUA}$ (-CA), runoff transcription of tRNAs, and the synthesis of misacylated tRNAs and of mRNAs were carried out as described (Lodder et al (1997) *J. Org. Chem.*, 62, 778–779; Mamaev et al (1996) *J Am. Chem. Soc.*, 118, 7243–7244).

In vitro suppression in a rabbit reticulocyte protein synthesizing system. In a typical experiment, DHFR was synthesized in reaction mixtures (20–100 µl total volume) that contained, per 100 µl; 70 µl of methionine-depleted, nuclease-treated rabbit reticulocyte lysate; 80 µCi of [$^{35}$S] methionine, 2 µl of 1 mM amino acid mixture (lacking methionine), 8 µg of mRNA and 10 µg of misacylated suppressor tRNA. Reactions were incubated at 30° C. for 1 h. In vitro translation of (control) pTHis15-derived mRNA was carried out without addition of misacylated tRNA. Aliquots (typically 1 µl) were utilized for analysis by 20% SDS-PAGE (Laemmli (1970) *Nature*, 227, 680–685). Autoradiography of the gels was carried out to determine the location of $^{35}$S labeled proteins; quantification of the bands was carried out using a phosphorimager. Five-ten µl aliquots from the reaction mixtures were used for the enzymatic assay.

In vitro suppression in an *E. coli* S-30 extract protein synthesizing system. The syntheses were carried out in reaction mixtures (25–100 µl total volume) that typically contained per 100 µl; 30 µl of S-30 extract, 40 µl of premix (Lesley et al. (1991) *J. Biol. Chem.*, 266, 2632–2638), 80 µCi of [$^{35}$S]methionine; 4 µl of 1 mM amino acid mixtures lacking methionine, 4 µl of 0.4 M Mg(OAc)$_2$, 4 µg of plasmid DNA linearized with BamHI, 200 units of T7 RNA polymerase and 10 µg of misacylated suppressor tRNA. Reactions were incubated at 37° C. for 1 h. In vitro translation of pTHis15-derived mRNA was carried out without addition of misacylated tRNA. Aliquots from the reaction mixtures (typically 5 µl) were withdrawn and precipitated with acetone for analysis by 20% SDS-PAGE, followed by autoradiography.

Purification of protein. In vitro translation mixture containing a $^{35}$S-labeled protein was loaded onto a Ni-NTA agarose column (200 µl) equilibrated with 50 mM sodium phosphate, pH 8.0, 300 mM NaCl, 20 mM imidazole and 100 µg/ml BSA. The column was washed with five 100 µl portions of this buffer, then the protein was eluded with five 100 µl portions of 50 mM sodium phosphate, pH 8.0, containing 300 mM NaCl, 250 mM imidazole, and 100 µg/ml BSA. The amount of $^{35}$S-abeled products in individual fractions was determined by liquid scintillation counting.

Results

Figure 1:
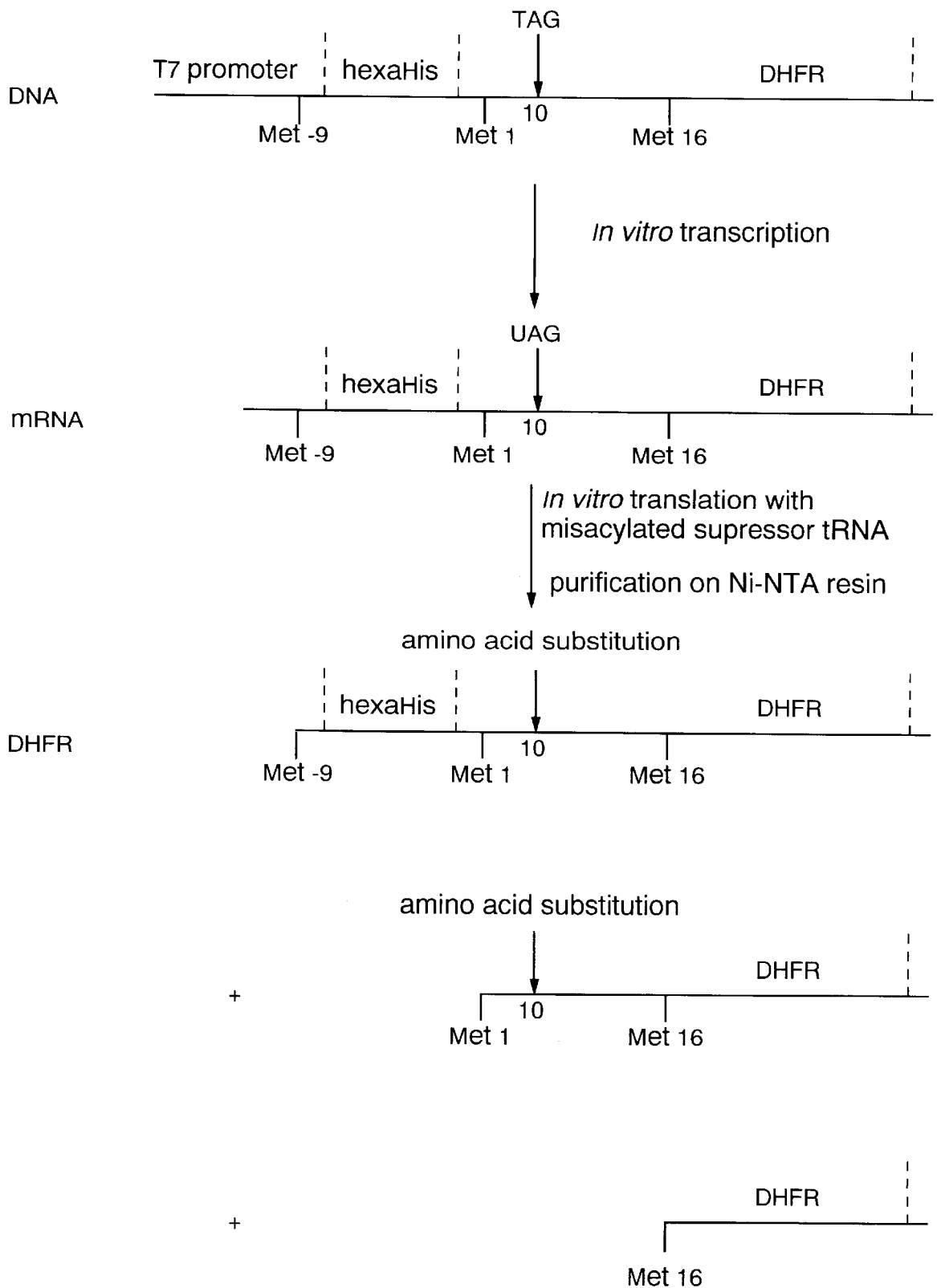
FIG. 1 shows the strategy employed for studying translation initiation. Linearized plasinid DNAs containing the DHFR gene with a stop codon (TAG) at positions 10 (as shown) or 27 were transcribed using T7 RNA polymerase. The DNA was modified to contain nucleotides encoding the nonapeptide MIHHHHHHE (Seq. ID No.: 1) immediately prior to the normal DHFR sequence and had ATG codons at positions -9, 1 and 16.

The general scheme used to study translation initiation is presented in FIG. 1. The scheme involved in vitro transcription of a linearized plasmid DNA containing a modified DHFR gene with three ATG codons (at positions -9, 1 and 16) and a stop codon (TAG) at position 10 (or 27). The derived mRNA was employed for in vitro translation in the presence of a misacylated suppressor tRNA. Because the DHFR gene was modified to encode a fusion nonapeptide at its N-terminus that includes hexahistidine, the fall length protein product could be purified on a Ni-NTA column (Janknecht et al (1991) *Proc. Natl. Acad. Sci. U.S.A.*, 88, 8972–8976). The requisite plasmids containing the modified DHFR genes, as well as two additional plasmids required as controls, have been constructed starting with plasmid pTZRKE (FIG. 2) (Karginov et al (1997) in preparation).

Figure 3:
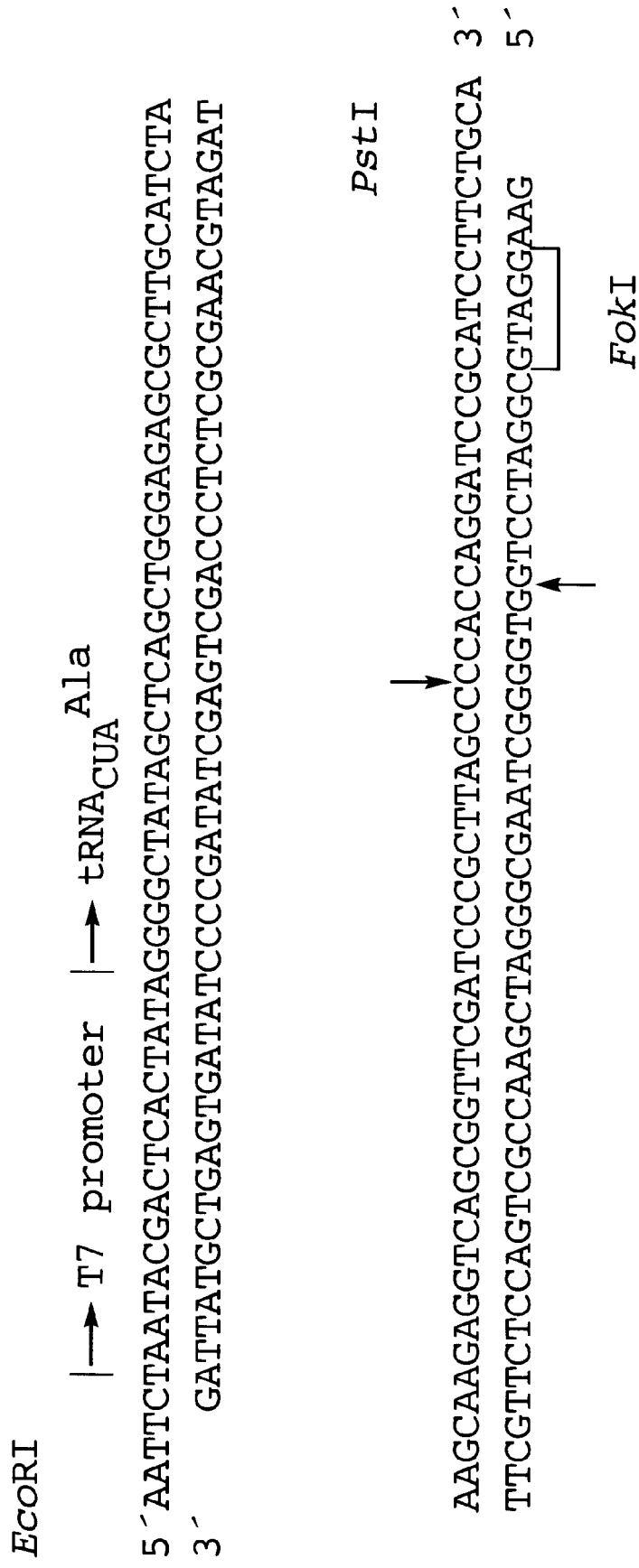
FIG. 3 depicts the DNA template used for in vitro runoff transcription of truncated $E.\ coli$ tRNA$^{Ala}_{CUA}$ (Seq. ID No: 2). The cleavage sites for FokI are indicated by arrows.

The truncated (-3' CA) suppressor tRNAs were synthesized by in vitro runoff transcription of the corresponding plasmid DNAs containing tRNA genes. Two kinds of suppressor tRNAs were tested for in vitro suppression; yeast tRNA$^{Phe}_{CUA}$ (Noren et al (1990) *Nucleic Acids Res.*, 18, 83–88; Sampson et al (1 988) *Proc. Natl. Acad. Sci. U.S.A.*, 85, 1033–1037) and *E. coli* tRNA$^{Ala}_{CUA}$ (Hou, Y. M et al (1988) *Nature*, 333, 140–145). The plasmid used for the runoff transcription of yeast tRNA$^{Phe}_{CUA}$ (–CA) was prepared by incorporation of the synthetic gene into plasmid pUC19 under the control of a T7 promoter. The construct employed for the elaboration of *E. coli* tRNA$^{Phe}_{CUA}$ (–CA) was prepared by incorporation of the synthetic gene into plasmid pUC19 under the control of a T7 promoter. The construct used for the elaboration of *E. coli* tRNA$^{Phe}_{CUA}$ gene was prepared by modification of the gene from plasmid pALA35. The final nucleotide sequence cloned into plasmid pSP65 is presented in FIG. 3. Both truncated tRNAs were synthesized in vitro by T7 RNA polymerase runoff transcription, then aminoacylated (Hecht et al (1978) *J. Biol. Chem.*, 253, 4517–4520; Heckler et al (1983) *J. Biol. Chem.*, 258, 4492–4495; Heckler et al (1984) *Biochemistry*, 23, 1468–1473; Baldini et al (1988) *Biochemistry*, 27, 7951–7959; Bain et al (1989) *J Am. Chem. Soc.*, 111, 8013–8014; Roesser et al (1989) *Biochemistry*, 28, 5185–5195; Robertson et al (1989) *Nucleic Acids Res.*, 17, 9649–9660; Noren et al (1990) *Nucleic Acids Res.*, 18, 83–88; Robertson et al (1991) *J. Am. Chem. Soc.*, 113, 2722–2729; Hecht (1992) *Acc Chem. Res.*, 25, 545–552; Lodder et al (1997) *J. Org. Chem.*, 62, 778–779), and subsequently used for in vitro suppression of UAG codons.

Figure 4:
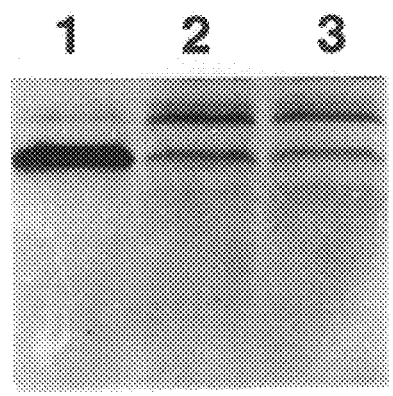
FIG. 4 is an autoradiogram of a 20% SDS-polyacrylamide gel illustrating the in vitro synthesis of [$^{35}$S] methionine-labled DHFR using an $E.\ coli$ S-30 extract coupled transcription—translation system as described under Materials and Methods. Lane 1, DHFR elaborated from pTHis 15 (wild-type) DNA; lane 2, DHFR expressed from pTZ27R2H11 (TAG027) DNA in the presence of $E.\ coli$ valyl-tRN$^{Ala}_{CUA}$; lane 3, DHFR elaborated from pTZ27R2H11 DNA in the presence of yeast valyl-tRNA$^{Phe}_{CUA}$. The band above the DHFR band is believed to be due to expression of β-lactamase from the plasmid.

In order to ensure that the suppression efficiency was not a strong function of the suppressor tRNA transcript employed, *E. coli* valyl-tRNAacuA and yeast valyl-tRNA$^{Phe}_{CUA}$ were compared for efficiency of in vitro suppression in a rabbit reticulocyte lysate translation system, as well as an *E. coli* S-30 coupled transcription—translation system. Both tRNAs exhibited about the same efficiency of suppression (~17%) in the presence of rabbit reticulocyte lysate (not shown) but the efficiency of suppression obtained with *E. coli* valyl-tRNA$^{Ala}_{CUA}$ was clearly better than that of the yeast suppressor tRNA (13% vs. 9%) in the S-30 system (FIG. 4).

Figure 5:
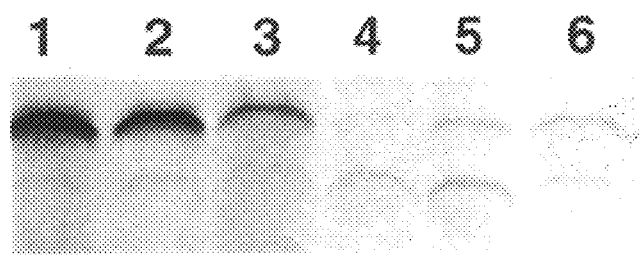
FIG. 5 shows the time dependence of [$^{35}$S]methionine-labeled DHFR synthesis, as judged by 20% SDS-PAGE. The DHFR was elaborated in rabbit reticulocyte lysate using plasmid pTZ27R2H11 DNA-derived mRNA and aspartyl-tRNA$^{Ala}_{CUA}$. Lane 1, 1 h; lane 2, 30 min.; lane 3, 15 min.; lane 4, 1 h (no aspartyl-tRNA$^{Ala}_{CUA}$); lane 5, 30 min. (no aspartyl-tRNA$_{CUA}$); lane 6, 15 min. (no aspartyl-tRNA$_{CUA}$).
Figure 6:
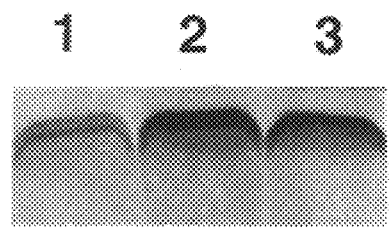
FIG. 6 shows the aminoacyl-tRNA concentration dependence of DHFR synthesis. Analysis of [$^{35}$S]methionine-labeled DHFR synthesized using pTZN2H4 DNA-derived mRNA and valyl-tRNA$^{Ala}_{CUA}$ was carried out by 20% SDS-PAGE. Lane 1, 0.02 mg/ml valyl-tRNA$_{CUA}$; lane 2, 0.1 mg/ml valyl-tRNA$_{CUA}$; lane 3, 0.2 mg/ml valyl-tRNA$_{CUA}$

Conditions optimal for protein synthesis as well as suppression of nonsense codons were determined by systematic variation of individual parameters; the experiments used to optimize reaction time and suppressor tRNA concentration are illustrated in FIGS. 5 and 6, respectively. As shown in FIG. 5, protein synthesis was essentially complete within one hour in agreement with earlier results (Resto et al (1992) *Nucleic Acids Res.*, 20, 5979–5983). The optimal concentration of valyl-tRNA$^{Ala}_{CUA}$ was found to be 0.1 mg/ml (FIG. 6).

Figure 7:
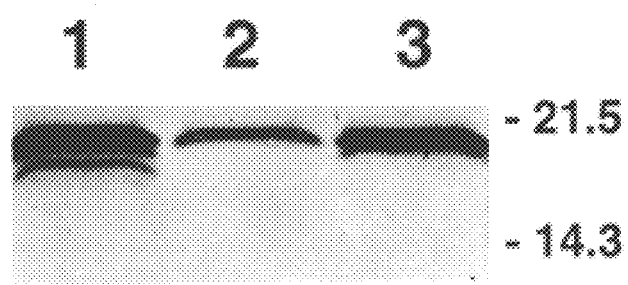
FIG. 7 depicts the elaboration and purification of DHFR. [$^{35}$S]methionine-labeled DHFR was prepared in the presence of pTZN2H4 DNA-derived mRNA and valyl-tRNA$^{Ala}_{CUA}$, then analyzed by 20% SDS-PAGE. Lane 1, crude DHFR derived from plasmid pTZN2H4 DNA; lane 2, DHFR derived from plasmid pTZN2H4 DNA then purified on Ni-NTA agarose; lane 3, crude DHFR derived from plasmid pTHis 15 DNA.

Synthesis of the nonapeptide-DHFR fusion product was carried out in the optimized rabbit reticulocyte system using mRNA prepared both from plasmid pTHis15 DNA (containing the wild-type DHFR gene) and plasmid pTZN2H4 DNA (containing a TAG codon at position 10) (FIG. 2). The latter synthesis employed valyl-tRNA$^{Ala}_{CUA}$ to effect suppression of the nonsense codon. Analysis of the in vitro translation products revealed that both reactions had afforded predominantly fill length protein product. However, a shorter by-product was apparent in the product mixture resulting from the wild-type mRNA (FIG. 7, lane 3) and two shorter by-products were present in the product mixture elaborated from the mRNA containing a stop codon at position 10 (FIG. 7, lane 1). Interestingly, the shorter by-products were not retained on the Ni-NTA column (FIG. 7, lane 2) indicating that these proteins lack part of the N-terminus of DHFR, including the fusion nonapeptide containing hexahistidine.

To facilitate a more detailed analysis of the nature of these protein products, an in vitro suppression reaction was carried out in the presence of decreasing amounts of misacylated valyl-tRNA$^{Ala}_{CUA}$. The products were separated by 20% SDS-PAGE (FIG. 8) and the amounts of proteins in the bands were determined using a phosphorimager. As shown in the figure, the ratio of full length DHFR (protein 1) to the larger of the two by-products was unaffected by the concentration of suppressor tRNA employed. In contrast, the production of the shorter by-product decreased by almost a factor of two, relative to full length DHFR, as the valyl-tRNA$^{Ala}_{CUA}$ concentration was increased from 0.02 to 0.1 mg/ml.

Discussion

We have previously described the over-expression of DHFR in a cell free system. The strategy involved initial gene amplification via the polymerase chain reaction, coupled with transcription and translation (GATT) (Resto et al (1992) Nucleic Acids Res., 20, 5979–5983). When employed with careful optimization of the transcription and translation reactions, ~$10^{10}$ copies of DHFR could be elaborated for each DNA$_{fol}$ used initially. The present study extends this work by defining conditions optimal for the read through of nonsense codon UAG in the rabbit reticulocyte lysate system, thereby facilitating the preparation of large quantities of proteins containing synthetic amino acids at predetermined sites (Noren et al (1989) Science, 244, 182–188; Ellman et al (1992) Methods Enzymol., 202, 301–336; Bain et al (1991) Tetrahedron, 47, 2389–2400; Bain et al (1991) Biochemistry, 30, 5411–5421; Bain et al (1992) Nature, 356, 537–539; Cornish et al (1995) Angew. Chem. Int. Ed. Engl., 34, 621–633; Mamaev et al (1996) J Am. Chem. Soc., 118, 7243–7244; Steward et al (1992) J Am. Chem. Soc., 119, 6–11).

Of particular interest was the finding during this optimization that an E. coli suppressor tRNA$^{Ala}_{CUA}$ described previously by Hou and Schimmel (Hou, Y. M et al (1988) Nature, 333, 140–145) could function well in protein synthesis as a suppressor tRNA following activation by "chemical aminoacylation" (Heckler et al (1983) J. Biol. Chem., 258, 4492–4495; Heckler et al (1984) Biochemistry, 23, 1468–1473; Hecht (1992) Acc Chem. Res., 25, 545–552). The ability of this tRNA to function in suppression could not be assessed in the earlier study because this tRNA is not a substrate for alanyl-tRNA synthetase; thus the present findings establish the ability of this species to function in the partial reactions of protein synthesis subsequent to aminoacylation. In addition to its favorable properties as a suppressor tRNA in comparison with other transcripts so employed (FIG. 4) (Noren et al (1990) Nucleic Acids Res., 18, 83–88), it seems unlikely that this tRNA$^{Ala}_{CUA}$ could be reactivated enzymatically by any endogenous aminoacyl-tRNA synthesis after transferring the synthetic amino acid introduced via chemical aminoacylation. This would thereby preclude the incorporation of a natural amino acid into a site in the protein intended for incorporation of a synthetic amino acid.

Initiation of protein synthesis in eukaryotes has been studied extensively (Kozak (1987) Nucleic Acids Res., 15, 8125–8148; Kozak (1989) J. Cell Biol., 108, 229–241; Kozak (1992) Crit. Rev. Biochem. Mol. Biol., 27, 385–402; Kozak (1986) Cell, 44, 283–292; Kozak (1987) J. Mol. Biol., 196, 947–950; Kozak (1989) Mol. Cell. Biol, 9, 5073–5080; Kozak (1987) Mol. Cell. Biol., 7, 3438–3445; Hinnebusch (1990) Trends Biochem. Sci., 15, 148–152; Kozak (1995) Proc. Natl. Acad. Sci. U.S.A., 92, 2662–2666). The scanning model (Kozak (1989) J. Cell Biol., 108, 229–241; Kozak (1992) Crit. Rev. Biochem. Mol. Biol., 27, 385–402; Kozak (1986) Cell, 44, 283–292; Kozak (1987) J. Mol. Biol., 196, 947–950; Kozak (1989) Mol. Cell. Biol., 9, 5073–5080) envisions entry of the 40S ribosomal subunit at the 5'-end of the mRNA, from which it travels linearly until the first AUG codon is encountered. Providing that this codon occurs in a favorable context, this AUG codon will constitute the unique site of translation initiation. Where the context in which this AUG codon occurs is suboptimal, it is postulated that some of the 40S ribosomal subunits may pass this codon and initiate translation at a downstream AUG codon. This process is termed "leaky scanning" (Kozak (1989) J. Cell Biol., 108, 229–241; Kozak (1992) Crit Rev. Biochem. Mol. Biol., 27, 385402; Kozak (1986) Cell, 44, 283–292; Kozak (1987) J. Mol Biol., 196, 947–950; Kozak (1989) Mol. Cell. Biol., 9, 5073–5080; Kozak (1995) Proc. Natl. Acad. Sci. U.S.A., 92, 2662–2666) and results in the synthesis of more than one protein from a single mRNA (Kozak (1991) J. Cell Biol., 115, 887–903; Lin (1993) Proc. Natl. Acad. Sci. U.S.A., 90, 9606–9610; Muralidhar et al (1994) J. Virol., 68, 170–176; Kozak (1994) Biochimie, 76, 815–821). A second mechanism by which a downstream AUG codon can be employed involves reinitiation of protein synthesis if the first AUG codon is followed by a termination codon (ozak (1987) Mol. Cell. Biol., 7, 3438–3445; Hinnebusch (1990) Trends Biochem. Sci., 15, 148–152).

Figure 8:
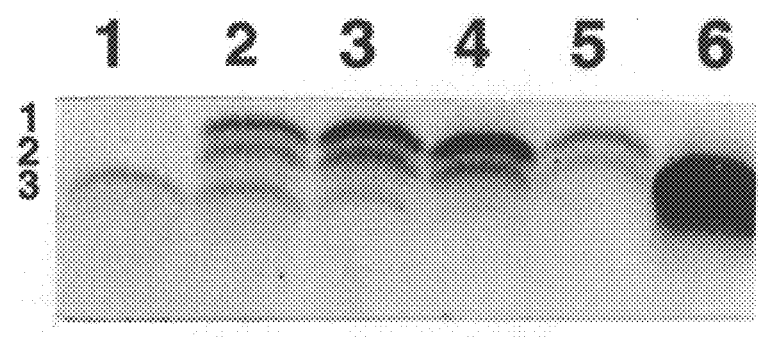
FIG. 8 shows the analysis of the synthesis of full length DHFR and shorter by-products as a function of valyl-tRNA$^{Ala}_{CUA}$ concentration. In Vitro synthesis of [$^{35}$S] methionine-labeled DHFR was carried out at three different concentrations using mRNA derived from plasmid pTZN2H4 DNA; the protein products were separated by 20% SDS-PAGE and then quantified using a phosphorimager. Lane 1, no valyl-tRNA; lane 2, 0.02 mg/mL of valyl-tRNA$_{CUA}$; lane 3, 0.05 mg/mL of valyl-tRNA$_{CUA}$; lane 4, 0.1 mg/mL of valyl-tRNA$_{CUA}$; lane 5, wild-type DHFR elaborated from plasmid pTHis 15 DNA-derived mRNA; lane 6, wild-type DHFR elaborated from plasmid pTZRKE DNA-derived mRNA.
Figure 9:
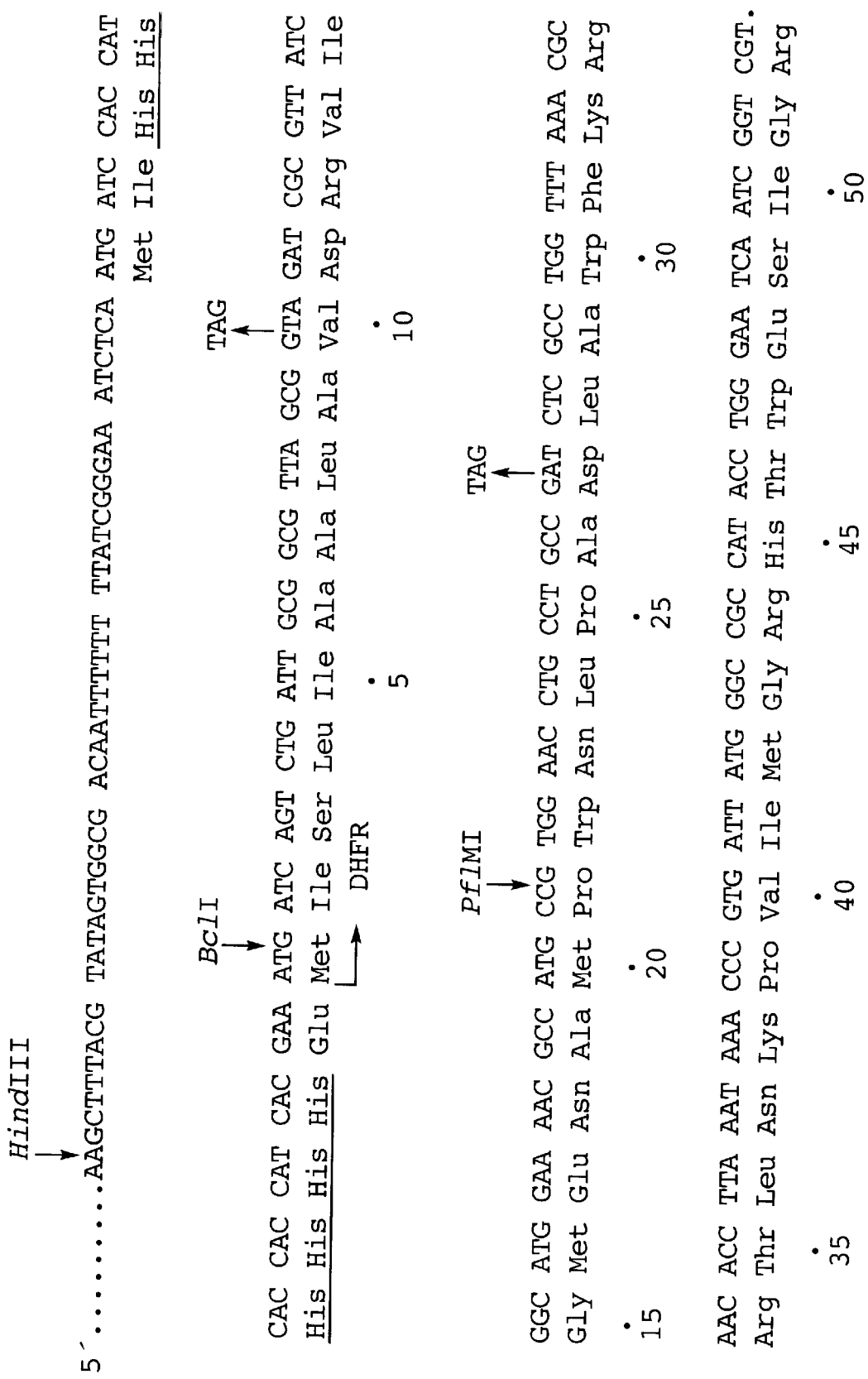
FIG. 9 is the nucleotide sequence and deduced amino acid sequence at the 5'-end of the DHFR gene SEQ ID NO: 3 and 4). Amino acids are numbered starting from the first Met of wild-type DHFR; a hexahistidine sequence added to the N-terminus to facilitate affinity purification is underlined. Restriction sites are indicated by arrows. Also indicated are the sites of introduction of nonsense codons (positions 10 and 27) and the start of the DHFR sequence (bold arrow).

The protein synthesizing system employed here for the elaboration of DHFR mutants at positions 10 and 27 provides a unique opportunity to observe both mechanisms for downstream initiation of protein synthesis operating simultaneously. Leaky scanning is possible due to the suboptimal context of the first AUG codon (FIG. 10) which, for example, lacks both a purine in position −3 and a G in position +4 (Kozak (1989) J. Cell Biol., 108, 229–241; Kozak (1992) Crit Rev. Biochem. Mol Biol., 27, 385–402; Kozak (1986) Cell, 44, 283–292; Kozak (1987) J. Mol Biol., 196, 947–950; Kozak (1989) Mol. Cell. Biol., 9, 5073–5080; Kozak (1995) Proc. Natl. Acad. Sci. U.S.A., 92, 2662–2666). As a consequence, a shorter protein can be translated from the second AUG codon; in the present case this would be the codon for Met-1 of wild-type DHFR. In fact the larger protein "by-product" (protein 2) evident in FIGS. 7 and 8 has properties entirely consistent with those that would be expected for the leaky scanning product. It co-migrates with DHFR lacking the hexahistidine fusion peptide (elaborated from plasmid pTZRKE; cf FIG. 8, lanes 2–4 and 6). This protein is present both in translation mixtures containing wild-type mRNA (FIG. 7, lane 3) as well as those containing mRNA with a stop codon in position 10 (FIG. 7, lane 1). As anticipated, this protein does not bind to Ni-NTA agarose. Further, the ratio between levels of expression of the full length DHFR product and protein 2 does not depend on concentration if misacylated tRNA in in vitro suppression reactions (FIG. 8).

The third product observed in the in vitro suppression reactions (protein 3) is obviously the result of the stop and reinitiation mechanism. It appears as the major band in the blank suppression reaction when no misacylated tRNA was added (FIG. 8, lane 1) and the level of its synthesis decreased with increasing concentrations of misacylated tRNA (FIG. 8). Like the leaky scanning product, protein 3 disappears after Ni-NTA chromatography. Because the first Met codon after the UAG codon at position 10 appears in position 16, this protein probably results from reinitiation of translation of Met-16; this is fully consistent with the relative mobilities of the full length and truncated proteins derived from PAGE experiments. Accordingly, the results presented above are fully consistent with the postulated rules of initiation of translation in eukaryotes.

The present system thus provides a very good model for qualitative and quantitative study of alternative mechanisms for initiation of translation. Both postulated mechanisms can be observed simultaneously, and can be controlled independently by judicious choice of codon contest (for the leaky scanning mechanism) and suppressor tRNA concentrations (for the reinitiation mechanism).

Example 2

Construction of Expression Plasmids and in Viro Transcription

Figure 11B:
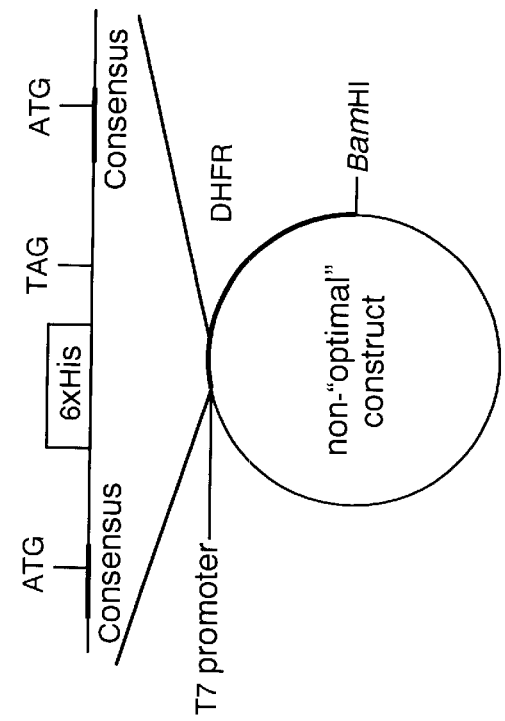
FIGS. 11A–D show plasmid DNA constructs for the in vitro translation of DHFR. (A) "Optimal" construct contains the first AUG codon in a favorable context (consensus sequence). (B) "Non-optimal" construct contains the first AUG codon in a suboptimal context (G in position +4 substituted to A, C in position -2 substituted to G, A in position -3 substituted to T). (C) "Poor" construct. First in-frame DHFR start codon overlaps with the stop codon of an upstream minicistron. (D) Plasmid pTHD8.
Figure 11D:
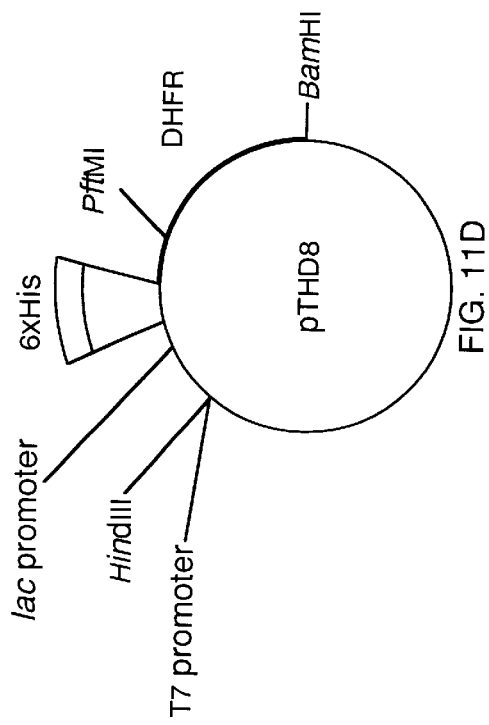
Figure 11A:
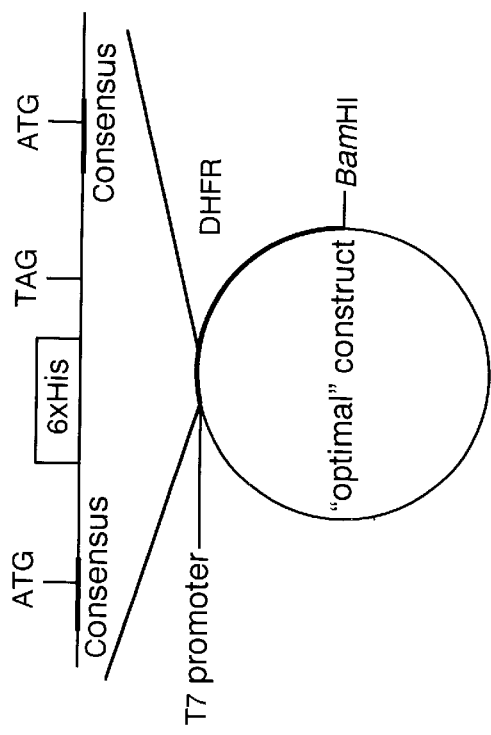
Figure 11C:
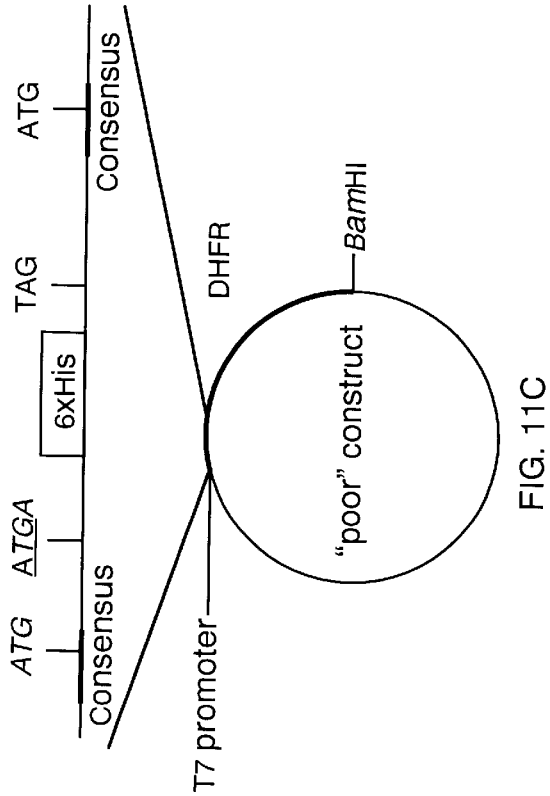

Three DNA constructs ("optimal", "non-optimal" and "poor") were created for the in vitro suppression experiments (FIGS. 11A, B, C). Each construct contained the DHFR gene under control of a T7 promoter. Two start codons for DHFR synthesis present in each mRNA synthesized from the plasmids. The first AUG codon for the "optimal" construct is in a favorable context, so translation should start very efficiently at that position. In the "non-optimal" construct, the first start codon is in a suboptimal context, so some 40S ribosomal subunits may pass it so that synthesis will start at the next AUG codon. The "poor" construct contains the first DHFR start codon in a position such that it overlaps with the termination TGA codon of an upstream minicistron. It has been shown by Kozak that translation starts at such positions very inefficiently (Kozak (1987) *Mol. Cell. Biol.*, 7, 3438–3445). For each of the constructs described a control (wild type) construct was created as well ("optimal/control", "non-optimal/control" and "poor/control"). The control constructs have the same structure as the suppression constructs, except that TAG codon used for suppression was changed to GCG.

Plasmid pTHD8 (FIG. 11D), coding for the gene for *E. coli* DHFR under control of a T7 promoter, was modified to obtain the desired DNA constructs. Six different sequences, coding for the first start codon of DHFR gene in a desired context, followed by the hexahistidine sequence, suppression stop codon (for suppression constructs), TEV protease cleavage site and first 19 amino acids of DHFR, were inserted into the plasmid by HindIII-PflMI restriction sites instead of the original fragment.

In vitro transcription of each of the six plasmids was carried out using T7 RNA polymerase, following linearization of the plasmid DNA with restriction endonuclease BamHI.

Preparation of $N^\alpha$-6-nitroveratryloxycarbonyl-$N^\beta$-(7-nitrobenz-2-oxa-1,3-diazol 4yl)-(S)-diaminopropionic Acid pdCpA Ester Mono-BOC protected diaminopropionic acid was converted to FMOC protected compound 3 in two steps in 82% yield. Introduction of an NVOC group by a reaction with NVOC chloride gave compound 4 which was converted to fluorescent compound 6 by removal of the FMOC group by treatment with piperidine, followed by a reaction with (7-nitrobenz-2-oxa-1,3-diazol4-yl) chloride. Compound 6 was treated with chloroacetonitrile to give compound 7 in 62% yield. Coupling of the activated ester with the tris (tetrabutylammonium) salt of pdCpA gave compound 8 in 39% yield.

In vitro Protein Synthesis

Figure 12:
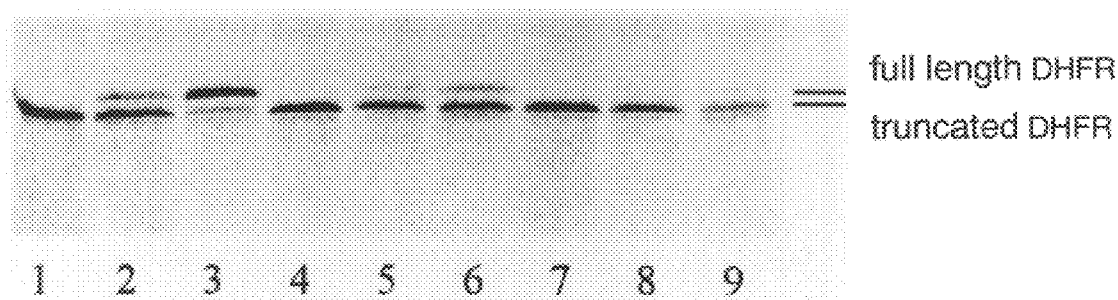
FIG. 12 shows in vitro synthesis of DHFR in the presence of valyl-tRNA$^{Phe}_{CUA}$. Protein synthesis was carried out in the presence of $^{35}$S-methionine using a rabbit reticulocyte lysate. Lane 1, translation of "poor/control" mRNA; lane 2, translation of "poor" mRNA in the presence of deprotected valyl-tRNA CUA; lane 3, translation of "poor" mRNA without valyl-tRNA$^{Phe}_{CUA}$; lane 4, translation of "non-optimal/control" mRNA; lane 5, translation of "non-optimal" mRNA in the presence of deprotected valyl-tRNA$^{Phe}_{CUA}$; lane 6, translation of "non-optimal" mRNA without valyl-tRNA$^{Phe}_{CUA}$; lane 7, translation of "optimal/control" mRNA; lane 8, translation of "optimal" mRNA in the presence of deprotected valyl-tRNA$^{Phe}_{CUA}$; lane 9, translation of "optimal" mRNA without valyl-tRNA$^{Phe}_{CUA}$.

In order to check translation and suppression efficiency for the constructs created, valyl-RNA$^{Phe}_{cuA}$ was employed in the first set of in vitro translation experiments (FIG. 12). Suppression efficiency and the ratio of full length: total DHFR protein produced (full length and truncated) for both control (wild type) and suppression constructs are presented on Table 1. As expected, for the "optimal" and "optimal/control" constructs, the amount of the full-length protein produced was much higher compared with "non-optimal" and "non-optimal/control" constructs. "Poor" and "poor/control" constructs produced extremely small amount of full length protein. Thus, the model system designed for monitoring alternative translation initiation showed the desired results and it was possible to measure translation initiation efficiency at different starting position by calculation of the ratio fill length to total protein produced. The calculation was performed by quantification of radioactivity from the polyacrylamide gel using a phosphorimager. Table 1. In vitro translation and suppression data for valyl-tRNA$^{Phe}_{CUA}$.

|  | Ratio of full length to total translation product | Suppression efficiency (%) |
| --- | --- | --- |
| optimal | 0.24 | 34 |
| non-optimal" | 0.11 | 40 |
| poor | not detected | not detected |
| optimal/control | 0.78 | |
| non-optimal/control | 0.21 | |
| poor/control | 0.11 | |

Figure 13:
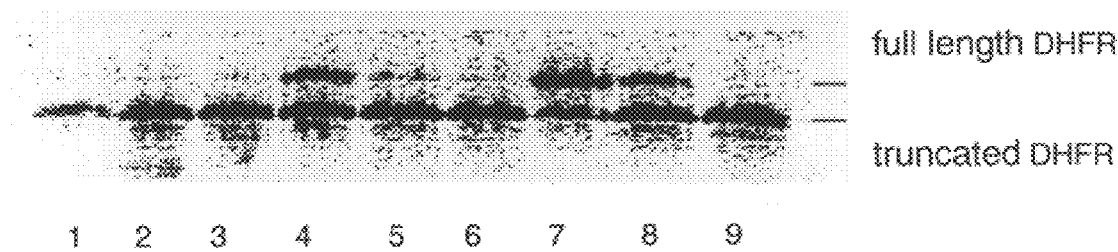
FIG. 13 shows in vitro translation of DHFR in the presence of NBD-Dap-tRNA$^{Phe}_{CUA}$ Protein synthesis was carried out in the presence of $^{35}$S-methionine using a rabbit reticulocyte lysate. Lane 1, translation of "poor/control" mRNA; lane 2, translation of "poor" mRNA in the presence of deprotected NBD-Dap-tRNA$^{Phe}_{CUA}$; lane 3, translation of "poor" mRNA in the presence of NVOC protected NBD-Dap-tRNA$^{Phe}_{CUA}$; lane 4, translation of "non-optimal/control" mRNA; lane 5, translation of "non-optimal" mRNA in the presence of deprotected NBD-Dap-tRNA$^{Phe}_{CUA}$; lane 6, translation of "non-optimal" mRNA in the presence of NVOC protected NBD-Dap-tRNA$^{Phe}_{CUA}$; lane 7, translation of "optimal/control" mRNA; lane 8, translation of "optimal" mRNA in the presence of deprotected NBD-Dap-tRNA$^{Phe}_{CUA}$; lane 9, translation of "optimal" mRNA in the presence of NVOC protected NBD-Dap-tRNA$^{Phe}_{CUA}$.

In vitro translation in the presence of suppressor tRNA$^{Phe}_{CUA}$ misacylated with NBD-Dap fluorescent amino acid showed the same results as for valyl-tRNA$^{Phe}_{CUA}$ (FIG. 13). Suppression efficiency was lower (Table 2), but the difference in the ratios of full length: total DHFR protein produced remained approximately the same. Table 2. In vitro translation and suppression data for NBD-Dap-tRNA$^{Phe}_{CUA}$.

|  | Ratio of full length to total translation product | Suppression efficiency (%) |
| --- | --- | --- |
| optimal | 0.13 | 21 |
| non-optimal | 0.05 | 11 |
| poor | not detected | not detected |

Figure 14:
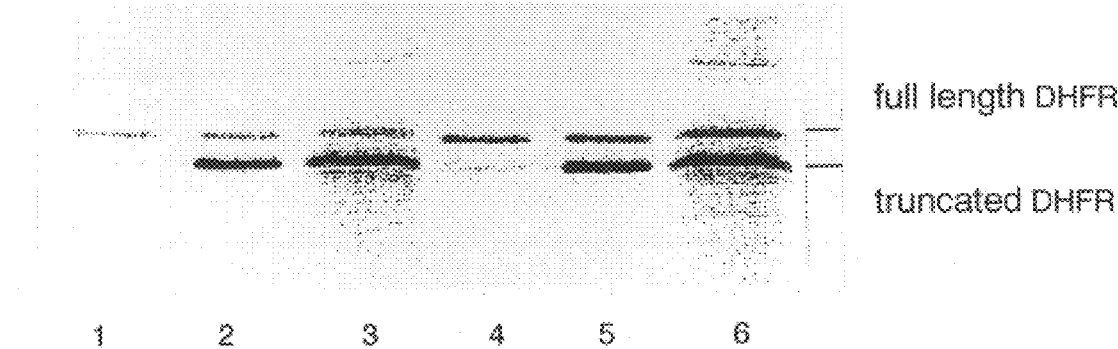
FIG. 14 shows the purification of "optimal" and "non-optimal" translation products. Lane 1, "nonoptimal" translation products purified on a Ni-NTA column; lane 2, "non-optimal"

Translation from "optimal" and "non-optima" RNAs in the presence of suppressor NBD-Dap-tRNA$^{Phe}_{CUA}$ was performed on a 1 ml scale. The products obtained were purified on DEAE Sepharose and Ni-NTA agarose (FIG. 14). It was necessary to purify the products from the excess of free fluorescent amino acid. DEAE Sepharose purification was carried out to remove hemoglobin (present in the rabbit reticulocyte lysate) from the mixture. The purification yield was approximately 90%.

The amount of the purified full-length "optimal" translation product was 3.5 times greater than for "non-optimal", which was in the approximately same proportion as in crude mixtures. The fluorescence emission spectra (excitation at 480 nm) of the purified materials were taken and normalized to the same baseline (FIG. 15). The peak at 575 nm, which was present in all spectra, is a background signal from scattered light. The translation products gave a fluorescent spectrum with the maximum at 557 nm, which correlates with the data for the free amino acid. The ratio of "optimal" to "non-optimal" fluorescent signal was 2:1. The ratio was obtained by subtracting the fluorescent signal for the control sample (purification of rabbit reticulocyte lysate mixed with pdCpA-NBD-Dap) from both the "optimal" and "nonoptimal" product spectra and comparison of fluorescence intensity values at 555 nm.

The ratio of fluorescent intensity to the total amount of the DHFR protein produced for "optimal" translation was 2.5 times greater than for "non-optimal". The ratio of full length to total translation product calculated by quantification of radiolabeled protein from the gel (data not shown) for "optimal" translation was 2.9 times greater than for "non-optimal".

The main concept was to model three different examples of alternative translation initiation and check the possibility of detecting and distinguishing translation efficiency from different start codons using in vitro suppression with a tRNA aminoacylated with a fluorescent amino acid. The results obtained for the designed constructs are in agreement with the current model of initiation of translation in eukaryotes (Kozak (1992) Crit Rev. Biochem. Mol. Biol., 27, 385–402). In vitro suppression experiments showed changes in translation initiation almost in the same proportion as it was shown for the wild-type constructs. The ratio of fluorescent signal to total translation product changed in the same proportion as the ratio of full length produced to total translation product. Therefore, this method is reliable enough to monitor translation initiation at different positions of an mRNA and to determine the efficiency of initiation. The use of a fluorescent amino acid in the in vitro suppression experiments make the analysis of the results easier and faster.

The system described can also be employed to study alternative translation initiation mechanisms and factors affecting translation initiation for numerous mammalian genes as well as for human immunodeficiency virus type 1 tat mRNA, hepatitis C virus (HCV), Moloney murine leukemia virus (MoMuLV), encephalomyocarditis virus (EMCV), foot-and-mouth disease virus (FMDV) and poliovirus mRNA.

Experimental Section

[$^{35}$S]Methionine (1000 Ci/mmol) was purchased from Amersham Corp. Nuclease-treated rabbit reticulocyte lysate system, T7 transcription kit and restriction endonucleases were obtained from Promega Inc. T4 DNA ligase and T4 RNA ligase were obtained from New England Biolabs. Synthetic oligonucleotides were obtained from Gibco BRL and Cruachem, Inc. Sequenase Version 2.0 DNA sequencing kit was purchased from USB. DEAE Sepharose CL-6B was obtained from Sigma Chemicals. NiNTA agarose was purchased from QIAGEN, Inc.

Ultraviolet spectral measurements were made using Perkin-Elmer Lambda Array 3840 spectrophotometer. Radioactivity measurements were made with a Beckman LS-100C liquid scintillation counter. Phosphorimager analysis was performed using a Molecular Dynamics 300E phosphorimager equipped with ImageQuant software. Fluorescent spectral measurements were made using Fluorolog 2 fluorescence spectrophotometer, Jobin Yvon SPEX, Inc.

Construction of Plasmids for DHFR Gene in Vitro Expression

Plasmid pTHD8, a derivative of pTZRKE plasmid (Karginov et al (1997) J. Am. Chem. Soc., 119, 8166–8176), encoding hexahistidine-DHFR fusion protein under control of T7 and lac promoters (FIG. 11D), was modified for this study. The HindIII-PflMI fragment from pTHD8 coding for lac-promoter, hexahistidine tag and first 19 amino acids of DHFR was replaced by synthetic oligonucleotide duplex, coding for hexahistidine tag, UAG site for suppression (for three suppression constructs) or GCG sequence (for wild type constructs), TEV-protease cleavage site, first 19 amino acids of DHFR and different 5'-untranslated regions, described in "Results and discussion" section. Totally 6 constructs were obtained. The plasmids were denoted pOpt3.3, pOC4.14, pNopt5.5, pNC2.4, pBad2.29, pBC5.1. The nucleotide sequences in all of the plasmids were verified by restriction analysis and Sanger DNA sequencing (Sanger et al (1977) Proc. Nat. Acad. Sci. USA, 74, 560–564).

In Vitro Transcription of tRNA

Plasmid pY8, encoding Yeast tRNA$^{Phe}_{CUA}$ (–CA) gene under control of T7 promoter (Karginove et al (1997) J Am. Chem. Soc., 119, 8166–8176), was linearized using FokI enzyme and then transcribed using a T7 transcription kit in buffered reaction mixture (100 μL total volume) containing 7.5 mM of each of the four NTPs, 10 mM dithiothreitol, 20 mM template DNA, 3000 units of T7 RNA polymerase, 150 units of Rnasine, 1.9 units of inorganic pyrophosphatase. The transcribed tRNA was recovered from the reaction mixture by precipitation with 2.5 volumes of ethanol, then collected by centrifigation and dried under vacuum. The crude tRNA was dissolved in 80% formamide containing 0.02% xylene cyanole and bromophenole blue, applied to an 8% polyacrylamide gel (40 cm×20 cm×2 mm), and subjected to electrophoresis at 800V for 3 hours. The tRNA band was visualized by UV shadowing, excised from the gel and recovered by crash and soak method (Maxam et al (1977) Proc. Natl. Acad. Sci. USA, 74, 560–564) with 100 mM Na acetate, pH 4.6, containing 1 mM EDTA and 0.01% SDS at 4° C. for 12 hours. The tRNA was precipitated with ethanol, dried and redissolved in water.

Synthesis of mRNA by in Vitro Transcription

The plasmid DNAs were linearized with BamHI restriction endonuclease and then transcribed with T7 transcription kit as described above for tRNA$^{Phe}_{CUA}$. mRNA was precipitated with equal volume of 6 M LiCl, to avoid precipitation of NTPs. The pellet was washed with 1 InL of 70% ethanol, dried and redissolved in water.

Synthesis of Misacylated tRNAs

Ligation reaction was carried out in 50 μL (total volume) of 50 mM HEPES-NaOH buffer, pH 7.5, containing 0.2 nmol of tRNA$^{Phe}_{CUA}$ (–CA), 0.5 A$_{260}$ unit (~20 mol) of an aminoacyl-pdCpA, 0.5 mM ATP, 15 mM MgCl$_2$, 10% dimethyl sulfoxide and 100 units of T4 RNA ligase. Reaction mixtures was incubated at 37° C. for 25 min and then quenched by the addition of 5 μL of 3 M Na acetate, pH 4.5. The (aminoacylated) tRNA was precipitated with 2.5 volumes of ethanol, collected by centrifugation, washed with 70% ethanol, and dried. The product was redissolved in 1 mM K acetate, pH 4.5 to a final concentration of 1 μL and then irradiated with a 500 W mercury-xenon lamp using Pyrex and water filters for 2 min to remove NVOC protection group. The deprotected aminoacyl-tRNA was used in in vitro suppression experiments immediately following deprotection.

The extent of ligation to afford misacylated tRNA was analyzed by electrophoresis on a (100×80×0.8 mm) 8% polyacrylamide gel containing 7 M urea in 100 mM Na acetate buffer, pH 4.5 at 200V for 2 hours.

In Vitro Synthesis of Dihydrofolate Reductase

In a typical experiment, DHR was synthesized in a reaction mixture (10–100 µL total volume) that contained per 100 µL: 70 µL of nuclease-treated rabbit reticulocyte lysate (for 50% rabbit reticulocyte lysate system 50 µL were added), 80 µCi of [$^{35}$S]-L-methionine (1000 Ci/mmol), 4 µL of 1 mM solution of all 20 amino acids, 5 µg of the appropriate mRNA, 20 µg of deprotected aminoacyl-tRNA$^{Phe}_{CUA}$. The reaction mixture was incubated at 30° C. for 1.5 hours. In vitro translation of control mRNAs was carried out without added misacylated tRNA. Aliquots (1 µL) were analyzed by 13% SDS-PAGE (Laemmli (1970) *Nature*, 227, 680–685). Analysis and quantification of bands was carried out using a phosphorimager.

Puirification of the Recombinant DHFR

In vitro translation mixtures (200 µL) containing $^{35}$S-labeled protein or 0.1 A$_{260}$ unit of NBD-Dap-pdCpA (control of purification) were incubated with 100 ng of RNase A for 30 min at room temperature and then applied to a DEAE Sepharose CL-6B column (200 µL) that had been equilibrated with 5 mM K phosphate buffer, pH 7.0. The column was washed with three 200 µL portions of 5 mM K phosphate buffer, pH 7.0. Remained proteins were eluted from the column with 200 µL of 5 mM K phosphate buffer, pH 7.0, containing 1 M KCl.

The eluted proteins were applied to a 50 µL Ni-NTA agarose column that had been equilibrated with 50 mM Na phosphate buffer, pH 8.0 containing 300 mM NaCl. The column was washed with four 400 µL portions of the same buffer. The protein was eluted with 200 µL of 50 mM Na phosphate buffer, pH 8.0 containing 300 mM NaCl and 50 mM EDTA. The amount of $^{35}$S-labeled protein was determined by liquid scintillation counting. Fluorescent spectra were taken at excitation wavelength 480 nm.

N$^{β}$-9-Fluorenylmethyloxycarbonyl-(S)-diaminopropionic Acid (3) (FIG. 16).

To a solution containing 750 mg (3.67 mmol) of N-butyloxycarbonyl-(S)-diaminopropionic acid (1) and 606 mg (3.67 mmol) of K$_2$CO$_3$ in 10 mL of H$_2$O and 5 mL of dioxane was added a solution of 1.36 g (4.04 mmol) of FMOC succinimide in 5 mL of dioxane. The mixture was stirred at room temperature for 24 h, diluted with 25 mL of H$_2$O, and washed with two 25-mL portions of ether. The aqueous phase was acidified to pH 2 with 1N NaHSO$_4$ and extracted with three 25-mL portions of CH$_2$Cl$_2$. The combined extract was dried (MgSO$_4$) and concentrated under diminished pressure. The crude compound 2 was dissolved in 9 mL of 4N HCl in dioxane. After stirring at room temperature for 2 h, the mixture was concentrated under diminished pressure. Crystallization from MeOH-ether gave N$^{β}$-9-fluorenylmethyloxycarbonyl-(S)diaminopropionic acid (3) as a fine colorless powder: yield 1.09 g (82%); mp 234–235° C.; $^1$H NMR (MeOD) δ 3.54 (dd, 1H, J=16 Hz, 6Hz), 3.68 (dd, 1H, J=14 Hz, 4 Hz), 4.02–4.04 (m, 1H), 4.17–4.19 (m, 1H), 4.32–4.36 (m, 2H), 7.25 (t, 2H, J=7 Hz), 7.34 (t, 2H, J=7 Hz), 7.60 (d, 2H, J=7 Hz), and 7.74 (d, 2H, J=7 Hz).

Anal. Calcd for C$_{18}$H$_{18}$N$_2$O$_4$Cl: C, 59.76; H, 5.02. Found: C, 59.57; H, 5.27.

Nα-6Nitroveratryloxycarbonyl-N$^{β}$-9-fluorenylmethyloxycarbonyl-(S)-diaminopropionic Acid (4)

To a solution containing 550 mg (1.52 mmol) of compound 3 and 502 mg (3.04 mmol) of K$_2$CO$_3$ in 5 mL of H$_2$O and 5 mL of dioxane was added 480 mg (1.74 mmol) of NVOC chloride. The mixture was stirred at room temperature for 17 h, diluted with 25 mL of 1N NaHSO$_4$ and extracted with three 25-mL portions of CH$_2$Cl$_2$. The organic extracts were dried (MgSO4) and concentrated under diminished pressure. Crystallization from acetone-hexanes gave compound 4 as a colorless solid: yield 673 mg (78%); mp 208–209° C.; $^1$H NMR (CDCl$_3$-MeOD) δ 3.25–3.45 (m, 2H), 3.67 (s, 3H), 3.69 (s, 3H) 3.92–4.18 (m, 4H), 5.23 (dd, 2H, J=10 Hz, 6 Hz), 6.84 (s, 1H), 7.07 (t, 2H, J =7 Hz) 7.14 (t, 2H, J=7 Hz), 7.34 (d, 2H, J=7 Hz), 7.43 (s, 1H), and 7.50 (d, 2H, J=7 Hz).

N$^{α}$-6Nitroveratryloxycarbonyl-N$^{β}$-(7-nitrobenz-2oxa-1,3diazol-4yl)-(S)-diaminopropionic Acid (6)

To a solution containing 250 mg (0.44 mmol) of compound 4 in 3 mL of CH$_2$Cl$_2$ was added 0.5 mL of piperidine. After stirring at room temperature for 45 min the mixture was concentrated under diminished pressure. The residue was precipitated from MeOH-ether and dried under diminished pressure to ensure complete removal of piperidine. The residue was suspended in 2 mL of H$_2$O and 4 mL of methanol and 74 mg (0.88 mmol) of NaHCO$_3$ was added, followed by 110 mg (0.55 mmol) of NBD chloride. After stirring at room temperature for 3 h another 100 mg portion of NBD chloride was added. After 16 h the mixture was diluted with 25 mL of 1N NaHSO$_4$ and extracted with three 25-mL portions of CH$_2$Cl$_2$. The combined extract was dried (MgSO$_4$) and concentrated under diminished pressure. The crude product was applied to a silica gel column (2×20 cm); elution with 3% acetic acid in ethyl acetate gave compound 6 as a orange solid: yield 60 mg (27%); $^1$H NMR (CDCl$_3$-MeOD) δ 3.09–3.11 (m, 2H), 3.70 (s, 3H), 3.71 (s, 3H), 4.29–4.31 (m, 1H), 5.25 (s, 2H), 6.17 (d, 1H, J=8 Hz), 6.83 (s, 1H), 7.46 (s, 1H), and 8.23 (d, 1H, J=8 Hz).

N$^{α}$-6-Nitroveratryloxycarbonyl-N$^{β}$-(7-nitrobenz-2oxa-1,3-diazol-4-yl)-(S-diaminopropionic Acid Cyanomethyl Ester (7)

To a solution containing 45 mg (0.089 mmol) of compound 6 in 2 mL of acetonitrile was added 62 µL (45 mg, 0.45 mmol) of triethylamine, followed by 56 µL (67 mg, 0.89 mmol) of chloroacetonitrile. After stirring at room temperature for 4 days the mixture was diluted with 25 mL of CH$_2$Cl$_2$ and washed with two 25-mL portions of 1N NaHSO$_4$. The organic layer was dried (MggSO4) and concentrated under diminished pressure. The crude product was applied to a silica gel column (1×10 cm); elution with ethyl acetate gave compound 7 as a yellow solid: yield 30 mg (62%); $^1$H NMR (acetone-d$_6$) δ 3.83 (s, 3H), 3.84 (s, 3H), 3.95–4.00 (m, 2H), 4.72–4.77 (m, 3H), 5.38 (s, 2H), 6.30 (d, 1H, J=9 Hz), 6.78 (d, 1H, J=7 Hz), 6.88 (s, 1H), 7.48 (br, 1H), 7.56 (s, 1H), and 8.35 (d, 1H, J=8 Hz).

N$^{α}$-6-Nitroveratryloxycarbonyl-N$^{β}$-(7-nitrobenz-2oxa-1,3-diazol-4-yl)-(S)-diaminopropionic Acid pdCpA Ester (8)

To a conical vial containing 4.0 mg (2.94 mmol) of the tris(tetrabutylammonium) salt of pdCpA was added 8.0 mg (14.7 mmol) of N$^{α}$-6-nitroveratryloxycarbonyl-N$^{β}$-(7-nitrobenz-2-oxa-1,3-diazol-4-yl)-(S)-diaminopropionic acid cyanomethyl ester (7) in 50 µL of DMF. The reaction mixture was stirred at room temperature for 16h. A 5-µL aliquot of the mixture was diluted with 45 µL of 1:1 CH$_3$CN-50 mM NH$_4$OAc, pH 4.5. Ten µL of the diluted aliquot was analyzed by HPLC on a C$_{18}$ reverse phase column (10×250 mm). The column was washed with 1→63% CH₃CN in 50 mM NH₄OAc, pH 4.5, over a period of 45 min at a flowrate of 3.5 mL/min (monitoring at 260 nm). The reaction mixture was diluted to a total volume of 500 μL of 1:1 CH₃CN-50 mM NH₄OAc, pH 4.5, and purified using the same semi-preparative C$_{18}$ reverse phase column (retention times 23.1 and 23.4 min for the two positional (2', 3') isomers). After lyophilization N$^\alpha$-6-nitroveratryloxycarbonyl-$^\beta$-(7-nitrobenz-2-oxa-1,3-diazol-4-yl)-(S)-diaminopropionic acid pdCpA ester (8) was obtained as a yellow solid: yield 1.3 mg (39%).

This application is based on Provisional Application, U.S. application Ser. No. 60/046,306, filed May 13, 1997, which is incorporated by reference herein in its entirety.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A rapid method for determining the use of different translation initiation sites of a nucleic acid encoding a protein, said method comprising:
   a) providing said nucleic acid, wherein the nucleic acid comprises
      a first and second stop codon, said first and second stop codon being seperate and distinct, and
      a first and second translation initiation site, wherein said first stop codon is positioned between said first translation site and said second translation initiation site, and said second stop codon is located downstream from the second translation initiation site;
   b) expressing proteins encoded by the nucleic acid in the presence of a suppressor tRNA misacylated with a labelled amino acid;
   c) determining the total amount of protein synthesized;
   d) determining the total amount of labelled protein synthesized, wherein the labelled protein represents the amount of protein translated from the first translation initiation site; and
   e) comparing the amount of labelled protein synthesized relative to the amount of protein synthesized to determine the relative use of the first and second translation initiation sites.

2. The method of claim 1, wherein the labelled amino acid is labelled with a reported moiety selected from the group consisting of flourescent moieties, chemiliminescent moieties, radioactive moieties, enzyme triggered color reporter moieties, and biotin.

3. The method of claim 2, wherein the labelled amino acid is labelled with a fluorescent moiety and the labelled protein is detected by measuring fluorescence.

4. The method of claim 2, wherein said misacylated suppressor tRNA is misacylated with 3-N-(7-nitrobenz-1-Oxa-1,3-diazol-4-yl)-2,3-diaminopropronic acid (NBD-Dap).

5. The method of claim 1, wherein said nucleic acid encodes dihydrofolate reductase (DHFR).

6. The method of claim 1, wherein said expression is performed in an in vitro translation system.

7. The method of claim 6, wherein said in vitro translation system comprises a rabbit reticulocyte lysate.

8. The method of claim 1, wherein step (b) comprises in vitro transcription of a plasmid DNA followed by in vitro translation of an mRNA produced by said transcription.

9. The method of claim 8, wherein said vitro transcription and translation system is an $E$ $coli$ S-30 couple transcription—translation system.

10. The method of claim 1, wherein the suppressor tRNA is yeast tRNA$^{Phe}_{CUA}$.

11. The method of claim 1, wherein the suppressor tRNA is $E$ $coli$ tRNA$^{Ala}_{CUA}$.

12. The method of claim 1, wherein the misacylated tRNA is used at a concentration of 0.1 mg/ml.

13. The method of claim 3, wherein the fluorescence is measured at 555 nm.

14. A rapid method for determining the use of different translation initiation sites of a nucleic acid encoding a protein, said method comprising:
   a) providing a linearized nucleic acid comprising a first and second translation initiation site and a stop codon, wherein the stop codon is positioned between said first translation initiation site and said second translation initiation site;
   b) expressing proteins encoded by the linearized nucleic acid in an in vitro runoff transcription-translation system and in the presence of a suppressor tRNA misacylated with a labelled amino acid;
   c) determining the total amount of protein synthesized;
   d) determining the total amount of labelled protein synthesized, wherein the labelled protein represents the amount of protein translated from the translation initiation site; and
   e) comparing the amount of labelled protein synthesized relative to the amount of protein synthesized to determine the relative use of the first and second translation initiation sites.

15. The method of claim 14, wherein the misacylated suppressor tRNA is labelled with a reporter moiety which is selected from the group consisting of fluorescent moieties, chemiluminescent moieties, radioactive moieties, enzyme triggered color reporter moieties and biotin.

16. The method of claim 15, wherein the misacylated suppressor tRNA is labelled with a fluorescent moiety and the labelled protein is detected by measuring fluorescence.

17. The method of claim 15, wherein said misacylated suppressor tRNA is misacylated with 3-N-(7-nitrobenz-1-oxa-1,3-diazol-4-yl)-2,3-diaminopropronic acid (NBD-Dap).

* * * * *